US011957780B2

(12) United States Patent
Sugimoto et al.

(10) Patent No.: US 11,957,780 B2
(45) Date of Patent: Apr. 16, 2024

(54) SKIN DULLNESS SUPPRESSING AGENT, AND SKIN BARRIER FUNCTION MAINTAINING OR IMPROVING AGENT

(71) Applicant: EZAKI GLICO CO., LTD., Osaka (JP)

(72) Inventors: Kazuhisa Sugimoto, Osaka (JP); Haruyo Sambe, Osaka (JP)

(73) Assignee: Ezaki Glico Co. Ltd., Osaka (JP)

( * ) Notice: Subject to any disclaimer, the term of this patent is extended or adjusted under 35 U.S.C. 154(b) by 70 days.

(21) Appl. No.: 17/449,701

(22) Filed: Oct. 1, 2021

(65) Prior Publication Data

US 2022/0016020 A1 Jan. 20, 2022

Related U.S. Application Data

(62) Division of application No. 16/613,743, filed as application No. PCT/JP2018/018632 on May 15, 2018, now abandoned.

(30) Foreign Application Priority Data

May 15, 2017 (JP) ................................ 2017-096146

(51) Int. Cl.

| | |
|---|---|
| ***A61K 36/67*** | (2006.01) |
| ***A61K 8/9789*** | (2017.01) |
| ***A61Q 17/00*** | (2006.01) |
| ***A61Q 19/00*** | (2006.01) |

(52) U.S. Cl.
CPC ............ *A61K 8/9789* (2017.08); *A61Q 17/00* (2013.01); *A61Q 19/00* (2013.01)

(58) Field of Classification Search
None
See application file for complete search history.

(56) References Cited

U.S. PATENT DOCUMENTS

| | | | |
|---|---|---|---|
| 2002/0032176 | A1 | 3/2002 | Maoka et al. |
| 2006/0185034 | A1 | 8/2006 | Todd et al. |
| 2012/0321730 | A1 | 12/2012 | Jacob et al. |

FOREIGN PATENT DOCUMENTS

| | | | |
|---|---|---|---|
| JP | H10-195433 | A | 7/1998 |
| JP | 2009-234925 | A | 10/2009 |

OTHER PUBLICATIONS

Fujifilm Corporation "Intake of the antioxidant component "astaxanthin" was verified to suppress ultraviolet-induced wrinkle formation on skin and water loss from the epidermis", dated Sep. 18, 2014 (in 3 pages).

*Primary Examiner* — Russell G Fiebig
(74) *Attorney, Agent, or Firm* — Knobbe, Martens, Olson & Bear LLP

(57) ABSTRACT

Provided is method of maintaining or improving a skin barrier function in a subject comprising orally administering to the subject a composition comprising an oil-soluble extract from red paprika, wherein the oil-soluble extract contains a hexane-soluble component.

12 Claims, No Drawings

SKIN DULLNESS SUPPRESSING AGENT, AND SKIN BARRIER FUNCTION MAINTAINING OR IMPROVING AGENT

TECHNICAL FIELD

The present invention relates to a skin dullness suppressing agent and a skin barrier function maintaining or improving agent. More specifically, the present invention relates to a skin dullness suppressing agent and a skin barrier function maintaining or improving agent, each of which contains an extract from red paprika.

BACKGROUND ART

The dullness of the skin is a phenomenon which occurs in the skin with ageing, and it is considered that the dullness of the skin is caused by combined effects of various factors such as the cloudiness or shading of the skin due to the thickening of a stratum corneum, the decrease in redness of the skin and the increase in yellowness of the skin. In the dull skin, the decrease in lightness is observed.

As a skin tone improving agent for improving the dullness of the skin, Patent Document 1 describes an oral preparation containing crocetin or a pharmacologically acceptable salt thereof as the active ingredient. Crocetin, which is the active ingredient of the oral preparation, can be produced by, for example, the extraction from a dried gardenia fruit with an ethanol-water mixed solution.

The deterioration in the skin barrier function is a phenomenon which often occurs in skin having various skin diseases or aged skin, and it is considered that the deterioration in the skin barrier function is caused by, for example, the structural or compositional defects of a stratum corneum for functioning the stratum corneum as a barrier. In the skin having deteriorated skin barrier function, the increase in the transepidermal loss of water contained in a lower layer of a stratum corneum is observed.

As a skin barrier function promotor, Patent Document 2 describes an external preparation containing one or both of tocopherol and a glyceride having a specified structure and astaxanthin. Astaxanthin to be contained in the external preparation can be produced, for example, as a Haematococcus algae extract.

As mentioned above, various attempts to use a plant-derived natural component as an active ingredient of a cosmetic have been made so far. On the other hand, a cosmetic utilizing a component derived from chili pepper (*Capsium annum* L.) is also known.

For example, Patent Document 3 discloses a fermented composition containing a fermented product of chili pepper or a capsinoid-containing plant or an extract from the fermented product. It is described that the fermented composition is preferably a fermented product of a non-pungent cultivar of chili pepper such as CH-19 sweet and can be used as an anti-fatigue agent, a physical strength increasing agent, an anti-obesity agent, an anti-oxidant agent, a skin beautifying agent, a skin whitening agent and a flavor improving agent.

Patent Document 4 describes a cosmetic composition containing an aqueous distillate produced by distilling at least one solanaceous plant selected from chili pepper and others with water vapor. It is described that the cosmetic composition can specifically improve dried skin and impart glow and elasticity to the skin.

Patent Document 5 describes a skin whitening cosmetic composition containing, as an active ingredient, at least one extract selected from an extract from wood ear mushroom that belongs to the family Auriculariaceae, an extract from Japanese horseradish (wasabi) that belongs to the family Brassicaceae, an extract from chili pepper that belongs to the family Solanaceae and an extract from buckwheat that belongs to the family Polygonaceae. In the skin whitening cosmetic composition, the extract from chili pepper that belongs to the family Solanaceae is produced from chili pepper which has been used as a spice, more specifically green chili pepper.

PRIOR ART DOCUMENTS

Patent Documents

Patent Document 1: Japanese Patent Laid-open Publication No. 2014-19692

Patent Document 2: International Publication No. 2011/074275

Patent Document 3: Japanese Patent Laid-open Publication No. 2005-161

Patent Document 4: Japanese Patent Laid-open Publication No. 2001-226219

Patent Document 5: Japanese Patent Laid-open Publication No. H5-163135

SUMMARY OF THE INVENTION

Problem to be Solved by the Invention

In the fermented composition disclosed in Patent Document 3, the pungent taste or acridity of the capsaicinoid is reduced and amino acids and vitamins are enriched by fermenting the raw material. As described in Comparative Examples 1 and 2 and others in Patent Document 3, the composition which is not fermented cannot achieve the desired effect. CH-19 sweet, which is a raw material that is confirmed to have the effect in Patent Document 3, is a kind of green non-pungent chili pepper.

In the cosmetic composition disclosed in Patent Document 4, an aqueous distillate produced by the distillation of chili pepper with water vapor is contained. Therefore, the active ingredient of the cosmetic composition is a water-soluble component among components derived from chili pepper. Furthermore, in the cosmetic composition, it is unknown as to whether the chili pepper is of a pungent type or a non-pungent type or whether the chili pepper is red chili pepper or green chili pepper.

In the skin whitening cosmetic composition disclosed in Patent Document 5, the active ingredient which is confirmed to have a skin whitening effect is an extract from green pungent chili pepper.

As described in Patent Documents 3 to 5, among components derived from chili pepper, a component derived from green chili pepper, a water-soluble component and/or a fermented component is actually confirmed to have an effect against the skin. The chemical composition of a component derived from chili pepper greatly varies depending on the type of the chili pepper, the extraction solvent to be used, the presence or absence of a fermentation treatment, and the like. With respect to components other than the above-mentioned components among the components derived from chili pepper, there is found no report about the fact that these components are inspected cosmetically. Furthermore, it is impossible to estimate as to whether or not these components have an effect against the dullness and an effect against the skin barrier function which are described in Patent Documents 1 and 2.

A main object of the present invention is to provide a novel plant-derived component-containing preparation having an effect against the dullness of the skin and an effect against a skin barrier function.

Means for Solving the Problem

As the result of the intensive and extensive studies, the present inventors have found that an oil-soluble extract from red paprika has an effect against the dullness of the skin and an effect against a skin barrier function. The present invention has accomplished by making further studies on the basis of this finding.

The present invention provides the following aspects of inventions.

1. A skin dullness suppressing agent including an oil-soluble extract from red paprika.

2. The skin dullness suppressing agent according to item 1, in which the skin dullness suppressing agent has a dosage form of an oral preparation.

3. The skin dullness suppressing agent according to item 1 or 2, in which the oil-soluble extract contains a hexane-soluble component.

4. A skin barrier function maintaining or improving agent including an oil-soluble extract from red paprika.

5. The skin barrier function maintaining or improving agent according to item 4, in which the skin barrier function maintaining or improving agent has a dosage form of an oral preparation.

6. The skin barrier function maintaining or improving agent according to item 4 or 5, in which the oil-soluble extract contains a hexane-soluble component.

7. A use of an oil-soluble extract from red paprika for production of a skin dullness suppressing agent.

8. A use of an oil-soluble extract from red paprika for production of a skin barrier function maintaining or improving agent.

Advantages of the Invention

According to the present invention, a novel plant-derived component-containing preparation having an effect against the dullness of the skin and an effect against a skin barrier function is provided.

EMBODIMENTS OF THE INVENTION

[1. Suppression of Dullness of Skin]

In a skin dullness suppressing agent according to the present invention, the term "skin dullness" (also simply referred to as "dullness", hereinafter) refers to a condition of the skin where the lightness of the skin is decreased. The dullness is caused by the thickening of a stratum corneum, the detachment of a stratum corneum, the deterioration in elasticity of the skin, the decrease in redness of skin tone, the increase in yellowness of skin tone and the like, and the mechanisms of action of these phenomena are different from the mechanism of action of pigmentation which is caused by the stimulation of a melanin cell.

In the dull skin, skin phenomena such as the decrease in transparency of the skin (turbidness of the skin), the decrease in glow of the skin (cloudiness of the skin) and the deposition of dirt such as sweat and sebum are observed. Examples of the factor that can cause the dullness include aging, environmental changes (including variation in atmospheric temperature, decrease in humidity and the like). These factors are often correlated with each other. Under the same environmental change, for example, the dullness suppressing effect of the dullness suppressing agent according to the present invention can be exerted more advantageously against more aged skin (e.g., skin of a 40-year-old or older person).

The dullness can be evaluated by measuring skin lightness (an L value). The skin lightness may decrease with the progression of dullness, while the skin lightness may increase with the improvement of dullness. The term "suppression of dullness" refers to an effect to fight back against the progression of dullness, and includes, for example, an effect to reduce the degree of decrease in skin lightness and an effect to maintain skin lightness both under a condition where dullness can be caused as well as an effect to increase skin lightness.

[2. Maintenance or Improvement of Skin Barrier Function]

With respect to the skin barrier function maintaining or improving agent according to the present invention, the term "skin barrier function" refers to a function produced as the result of the adhesion of a corneocyte to a horny layer intercellular lipid in a stratum corneum or the like. The skin phenomenon that the skin barrier function is deteriorated is caused as the result of the disorder of the arrangement of corneocytes due to the deterioration in adhesion between the corneocytes and a horny layer intercellular lipid or the like, and the mechanism of action thereof is different from that of the deterioration in the proliferation function of fibroblasts and is also different from that of sunburn-induced transient inflammation.

In the skin having deteriorated skin barrier function, the water loss from an under layer of a stratum corneum increases to increase the sensitivity to an external stimulus. As a result, a skin phenomenon such as roughening of skin, rash and itching is observed. As the factors that can cause the deterioration in skin barrier function, aging, environmental changes (including variation in atmospheric temperature, decrease in humidity and the like), stress, an environmental pollutant and the like can be mentioned. These factors are often correlated with each other. The skin barrier function maintaining or improving effect by the skin barrier function maintaining or improving agent according to the present invention can be exerted more advantageously against the skin of a person in a younger to middle age group (e.g., a person of 30 years of age or older and 40 years of age or younger) who is especially sensitive to a factor that may cause the deterioration in a skin barrier function.

The skin barrier function can be evaluated in terms of a transepidermal water loss (TEWL). When the skin barrier function is deteriorated, the transepidermal water loss tends to be increased. When the skin barrier function is improved, in contrast, the transepidermal water loss tends to be decreased. The term "maintenance or improvement in skin barrier function" refers to an effect to prevent the deterioration of skin barrier function, and includes, for example, an effect to reduce the degree of increase in transepidermal water loss and an effect to maintain transepidermal water loss both under a condition where the deterioration in skin barrier function can be caused as well as an effect to decrease transepidermal water loss.

[3. Extract from Red Paprika]

Each of the skin dullness suppressing agent and the skin barrier function maintaining or improving agent according to the present invention contains an oil-soluble extract derived from red paprika as an active ingredient. The extract from red paprika is an extract produced by carrying out an extraction treatment of red paprika.

[3.1 Raw Materials]

Red paprika is a plant belonging to the family Solanaceae, the genus *Capsicum*. Red paprika is specifically *Capsicum annuum*, more specifically *Capsicum annuum* L., still more specifically *Capsicum annuum* L. var. *grossium*. Among the above-mentioned plants, red paprika is a non-pungent cultivar of chili pepper having a red color. The cultivar, the production area and the like of red paprika are not particularly limited. Examples of the cultivar of red paprika include bell-shaped paprika, ramyuro-type paprika, and wedge-shaped paprika (palermo). From the viewpoint of the production efficiency of the extract, a cultivar having a smaller water content (e.g., wedge-shaped paprika such as palermo) is preferred.

The extraction part in red paprika is not particularly limited, as long as at least a fruit pulp part is contained. Examples of another part that is acceptable as the extraction part include a seed, a flower, a stem, a leaf and a rhizome. From the viewpoint of advantageously achieving the dullness suppressing performance and skin barrier function maintaining or improving performance, it is preferred that the extraction part is substantially only a fruit pulp part. In the production of the extract, the extraction part in red paprika may be used without any modification, or may be used in a pretreated state, for example such a state that the part is milled or finely cut in advance or the part is dried and then is milled or finely cut.

[3-2. Extraction]

The extraction method is not particularly limited, as long as an organic solvent is used as the extraction solvent. The organic solvent may be any one of a non-polar solvent, a polar aprotic solvent and a polar protic solvent. Examples of the non-polar solvent include: a hydrocarbon-type solvent such as hexane (e.g., n-hexane, cyclohexane) and toluene, preferably hexane (n-hexane, cyclohexane), particularly preferably n-hexane; an ether-type solvent such as dimethyl ether and diethyl ether; a halogenated hydrocarbon-type solvent such as chloroform, methylene chloride and trichloroethylene; and an ester-type solvent such as ethyl acetate. An example of the polar aprotic solvent is a ketone-type solvent such as acetone. An example of the polar protic solvent is an alcohol-type solvent such as methanol, ethanol, n-propanol and isopropanol, preferably ethanol.

The above-mentioned organic solvents may be used singly, or a combination of two or more of them may be used. From the viewpoint of advantageously achieving the dullness suppressing performance and the skin barrier function maintaining or improving performance, the organic solvent may contain at least a non-polar solvent, preferably a hydrocarbon-type solvent, more preferably n-hexane, in an amount of, for example, 1 to 100% by volume, preferably 30 to 100% by volume, therein.

From the viewpoint of concentration efficiency, the organic solvent may have a boiling point of 80° C. or lower, preferably 70° C. or lower.

With respect to the extraction operation, it may be possible, for example, to immerse red paprika in the organic solvent by cold immersion, hot immersion or the like, and optionally stir or homogenize the immersed product to thereby elute an active ingredient in the organic solvent. Examples of the organic solvent include hexane, acetone and ethanol. From the viewpoint of the extraction efficiency and the achievement of the dullness suppressing performance and the skin barrier function maintaining or improving performance, it is preferred to use at least hexane. The conditions to be employed for the elution are not particularly limited. The amount of the organic solvent is 1- to 20-fold weight, preferably 2- to 10-fold weight, in terms of a dry weight of the extraction part, the temperature is, for example, 10° C. to 50° C., preferably 20° C. to 30° C., and the time is 1 hour to 72 hours, preferably 4 hours to 48 hours.

The organic solvent fraction can be separated by solid-liquid separation. The method for the separation is not particularly limited, and may be selected appropriately from a column separation method, a filtration method and a centrifugal separation method. The separated organic solvent fraction may be concentrated by removing a portion or the whole of the organic solvent. A liquid concentrate thus produced or a concentrate that is a dried product of the liquid concentrate can be obtained as the red paprika extract. The dried product can be obtained by a drying treatment such as concentration to dryness, atomization to dryness and lyophilization. The red paprika extract may be produced by further carrying out a purification treatment or a separation treatment of a highly active fraction, as required. Examples of the purification treatment include treatments such as filtration, adsorption (e.g., an ion exchange resin column, an activated carbon column) Examples of the treatment for the separation of the highly active fraction include gel filtration, an adsorption treatment, silica gel column chromatography and HPLC.

From the viewpoint of achieving the dullness suppressing performance and the skin barrier function maintaining or improving performance, the extract does not undergo a decomposition treatment such as fermentation. Furthermore, it is preferred that the extract does not undergo any treatment accompanied by chemical change other than a decomposition treatment, either.

[3-3. Components]

Since the raw material for the extract according to the present invention is red paprika which is non-pungent chili pepper, a pungent component is not contained in a substantial amount (i.e., an amount at which a pungent flavor or irritation can be produced as in the case of a pungent chili pepper component). An example of the pungent component is a capsaicinoid contained in pungent chili pepper, more specifically capsaicin, dihydrocapsaicin, nordihydrocapsaicin, homocapsaicin, homodihydrocapsaicin or the like.

Furthermore, the red paprika extract is oil-soluble. The term "oil-soluble" as used herein refers to a property to be insoluble in water. The oil-soluble extract should contain a component soluble in an organic solvent. Examples of the organic solvent are those organic solvents which are mentioned above as the extraction solvents. Therefore, examples of the component soluble in the organic solvent include: a component soluble in a non-polar solvent, including a component soluble in a hydrocarbon-type solvent such as hexane (e.g., n-hexane, cyclohexane) and toluene, preferably hexane (n-hexane, cyclohexane), particularly preferably n-hexane, a component soluble in an ether-type solvent such as dimethyl ether and diethyl ether, a component soluble in a halogenated hydrocarbon-type solvent such as chloroform, methylene chloride and trichloroethylene, and a component soluble in an ester-type solvent such as ethyl acetate; a component soluble in a polar aprotic solvent, including a component soluble in a ketone-type solvent such as acetone; and a component soluble in a polar protic solvent, including a component soluble in an alcohol-type solvent such as methanol, ethanol, n-propanol, isopropanol, preferably ethanol.

In the above-mentioned oil-soluble extract, the above-mentioned soluble components may be contained singly or two or more of them may be contained in combination. From the viewpoint of advantageously achieving the dullness suppressing performance and the skin barrier function maintaining or improving performance, it is preferred to contain at least a component soluble in a non-polar solvent, preferably a component soluble in a hydrocarbon-type solvent, more preferably a component soluble in hexane, particularly preferably a component soluble in n-hexane, among the above-mentioned soluble components.

More specific examples of the component to be contained in the oil-soluble extract include xanthophyll and β-carotene. Examples of the xanthophyll include capsanthin, cucurbitaxanthin A, β-cryptoxanthin, zeaxanthin, capsanthin 3, 6-epoxide, capsorubin, cryptocapsin and derivatives thereof. An example of the derivative is a fatty acid ester. A specific example of the fatty acid ester is an ester of a saturated or saturated fatty acid having 12 to 22 carbon atoms such as lauric acid, myristic acid, palmitic acid, stearic acid and oleic acid.

From the viewpoint of achieving the dullness suppressing performance and the skin barrier function maintaining or improving performance, the oil-soluble extract may have a color value ($E^{10\%}_{1cm}$) of, for example, 300 to 3500, preferably 1000 to 3500. In the present invention, the term "color value ($E^{10\%}_{1cm}$)" refers to a numerical value determined by measuring an absorbance at a maximum absorption wavelength (460 nm) in a visible part of an acetone solution containing an oil-soluble extract of interest and then converting the absorbance to an absorbance of a 10-w/v % acetone solution.

[4. Dullness Suppressing Agent and Skin Barrier Function Maintaining or Improving Agent]

The skin dullness suppressing agent or the skin barrier function maintaining or improving agent should contain at least the above-mentioned oil-soluble extract. The skin dullness suppressing agent and the skin barrier function maintaining or improving agent may be prepared in the form of a composition that further contains an additive suitable for a dosage form capable of being applied to a living body.

[4.1 Application Embodiments]

Examples of the application embodiments of the dullness suppressing agent or the skin barrier function maintaining or improving agent include an external preparation for skin, an oral preparation, a transvenous preparation, a transarterial preparation, a subcutaneous preparation and an intramuscular preparation. Among these application embodiments, an external preparation for skin and an oral preparation are preferred, and an oral preparation is more preferred from the viewpoint of convenience and the efficient achievement of the dullness suppressing performance or the skin barrier function maintaining or improving performance.

[4.2 Subject to be Applied]

Examples of the subject to be applied with the dullness suppressing agent according to the present invention include a subject who has an awareness of dullness and needs to be suppressed from the progression of dullness or needs to be improved in dullness, and a subject who needs to be prevented from dullness. The subject to be applied with the dullness suppressing agent is preferably a subject in an older age group, more specifically a subject of 40 years of age or older.

Examples of the subject to be applied with the skin barrier function maintaining or improving agent according to the present invention include a subject who has an awareness of the deterioration in a skin barrier function and needs to be suppressed from the deterioration in a skin barrier function or needs to be improved in the deterioration in a skin barrier function, and a subject who needs to be prevented from the deterioration in a skin barrier function. The subject to be applied with the skin barrier function maintaining or improving agent is preferably a subject in a younger to middle age group who is especially sensitive to a factor that can cause the deterioration in a skin barrier function, more specifically a subject of 30 years of age or older and 40 years of age or younger.

[4.3 Appearance]

Examples of the appearance of the dullness suppressing agent and the skin barrier function maintaining or improving agent include a solid form (e.g., a powdery form, a granular form, a tablet), a liquid form (e.g., a form prepared by dissolving or dispersing in an oil, water or another solvent), and a semi-solid form (e.g., a gel-like form, an ointment-like form and a paste-like form prepared by dispersing in an oil, water or another solvent).

[4.4 External Preparation for Skin]

In an external composition for skin to be used as an external preparation for skin, a pharmacologically, cosmetologically and pharmaceutically acceptable additive may be added. The additive may be selected depending on the type of the preparation form and the formulation form, and examples of the additive include an excipient, a thickening agent, a tonicity agent, a pH adjuster, a stabilizing agent, an antiseptic agent, a preservative agent, a dispersing agent, an emulsifying agent, a gelatinizing agent, a pigment and a perfume material. Examples of the type of the preparation form include a liquid oil form, an emulsion form, a powdery form, a powder dispersion form, a gel form, an ointment form, an aerosol form, a water-oil bilayer form, and a water-oil-powder trilayer form. The formulation form of the external composition for skin is not particularly limited, as long as the formulation form can be applied transepidermally, and examples of the formulation form include a drug for external application to skin, a quasi-drug for external application to skin, a cosmetic and a skin cleanser. More specific examples of the formulation form include: a drug for external application to skin, such as a cream, a lotion, a gel, an emulsion, a solution, an adhesive patch, an aerosol, an ointment and a pack; a quasi-drug for external application to skin, such as a cream, a lotion, a gel, an emulsion, a solution, an adhesive patch, an aerosol, an ointment and a pack; a cosmetic, such as a cream, a lotion, a gel, an emulsion, a solution, an ointment and a pack; and a skin cleanser, such as body shampoo, hair shampoo and hair conditioner. Among these formulation forms, a drug for external application to skin is preferred, and a cream, a lotion, a gel, an emulsion or a pack is more preferred.

The amount (in terms of a dry weight) of the oil-soluble extract to be contained in 100% by mass of the dullness suppressing agent and the skin function maintaining or improving agent to be used as an external composition for skin (external preparation) may be, for example, 0.005% by mass to 100% by mass, preferably 0.02% by mass to 100% by mass. In the present invention, the term "a value in terms of a dry weight" refers to a value of the amount of the oil-soluble red paprika extract which is determined in terms of a dry weight (i.e., an amount of a dried solid matter). When other components such as a solvent and an additive are contained in the composition, the value corresponds to a weight of the composition from which the amounts of the above-mentioned other components are subtracted.

The amount of the oil-soluble extract in the dullness suppressing agent and the skin barrier function maintaining or improving agent to be used as an external composition for skin (external preparation) may be such an amount that the color value ($E^{10\%}_{1cm}$) of the composition can become 0.1 to 3500, preferably 0.5 to 3500.

The dose amount of the dullness suppressing agent and the skin barrier function maintaining or improving agent to be used as an external composition for skin (external preparation) may be adjusted appropriately depending on the type of the preparation form, the formulation form, the level of the condition of skin to which the preparation is to be applied and the like. As a specific example of the dose amount, the agent is applied in a single dose or about several divided doses per day in such an amount that, for example, the amount (in terms of a dry weight) of the oil-soluble extract can become 0.1 μg to 6 μg/dose, preferably 0.4 μg to 3 μg/dose, per 1 $cm^2$ of skin.

As another specific example of the dose amount of the dullness suppressing agent and the skin barrier function maintaining or improving agent to be used as an external composition for skin (external preparation), the agent is applied in a single dose or about several divided doses per day in such an amount that the total color value amount (($E^{10\%}_{1cm}$)×weight (g)) can become, for example, 0.0004 to 0.02/dose, preferably 0.001 to 0.008/dose, per 1 $cm^2$ of skin.

[4.5 Oral Preparation]

Examples of the oral composition to be used as an oral preparation include foods and beverages, including a health food, a functional food, a dietary supplement and a food for specified health use. In the oral composition, a food-hygienically acceptable additive may be added. Examples of the additive include; a sweetener such as glucose, sucrose, fructose, high-fructose corn syrup, aspartame and stevia; an acidulant such as citric acid, malic acid and tartaric acid; an excipient such as dextrin and starch; a binder; a diluent such as an oil and a fat; a flavoring material; a coloring agent; a buffering agent; a thickening agent; a gelatinizing agent; a stabilizing agent; a preservative agent; an emulsifying agent; a dispersing agent; a suspending agent; and an antiseptic agent. Examples of the dosage form of the dullness suppressing agent and the skin barrier function maintaining or improving agent to be used as an oral composition include; a supplement such as tablets, hard capsules and soft capsules; various beverages (e.g., a refreshing beverage, a carbonated beverage, a beauty drink, a nutritional beverage, a fruit beverage, a milk beverage); an original liquid concentrate or an instant powder for each of these beverages; an oil and a fat, and oil and fat processed food; and a seasoning agent.

The amount (in terms of a dry weight) of the oil-soluble extract to be contained in 100% by mass of the dullness suppressing agent and the skin barrier function maintaining or improving agent to be used as an oral composition (oral preparation) may be, for example, 0.005% by mass to 100% by mass, preferably 0.01% by mass to 100% by mass.

The amount of the oil-soluble extract to be contained in the dullness suppressing agent and the skin barrier function maintaining or improving agent to be used as an oral composition (oral preparation) may be such an amount that the color value ($E^{10\%}_{1cm}$) of the composition can become 0.1 to 3500, preferably 0.2 to 3500.

The dose amount of the dullness suppressing agent and the skin barrier function maintaining or improving agent to be used as an oral composition (oral preparation) may be adjusted appropriately depending on the type of the preparation form, the formulation form, the level of the condition of skin to which the preparation is to be applied and the like. As a specific example of the dose amount, the agent is applied in a single dose or about several divided doses per day in such an amount that the amount (in terms of a dry weight) of the oil-soluble extract can become, for example, 10 mg to 400 mg/day, preferably 50 mg to 200 mg/day.

As another specific example of the dose amount of the dullness suppressing agent and the skin barrier function maintaining or improving agent to be used as an oral composition (oral preparation), the agent is applied in a single dose or about several divided doses per day in such an amount that the total color value amount (($E^{10\%}_{1cm}$) weight (g)) can become, for example, 30 to 1000/day, preferably 200 to 500/day.

EXAMPLES

Example 1

As a raw material, 5 g (in terms of dry weight) of red paprika (palermo, a European cultivar) was provided. The dried red paprika was cut into fine pieces, then the fine pieces were immersed in a 6-fold weight of n-hexane at room temperature for 21 hours, and then the resultant solution was filtrated to separate an n-hexane fraction. n-Hexane was removed by distillation under a reduced pressure to produce an oily extract. The extract thus produced had a color value ($E^{10\%}_{1cm}$) of 660. The color value was determined by preparing a solution by diluting the extract with acetone, then measuring an absorbance of the solution at a maximum absorption wavelength (460 nm) in a visible part of the solution using an ultraviolet-visible spectrophotometer (V-650, manufactured by JASCO Corporation), and then converting the absorbance to an absorbance of a 10-w/v % acetone solution.

Example 2

Red paprika extract-containing soft capsules (having a total color value amount of 270 per capsule) each containing 333 mg of a commercially available red paprika oil-soluble extract preparation having a color value of 810 (PapriX; manufactured by Glico Nutrition Co., Ltd.) were prepared. Forty three normal male and female persons were divided into a test food ingestion group (22 persons) and a placebo food ingestion group (21 persons). The range of the ages of the whole population of the forty three normal male and female persons was 30 to 49 years old, the average of the ages was 41.1 years old, and the median of the ages was 41 years old. In the test food ingestion group, the red paprika extract-containing soft capsules were ingested every day at a dose of 1 capsule/day over two weeks. In the placebo food ingestion group, soft capsules, which contained the same components as those of the test food except that the red paprika extract was not contained, were ingested every day at a dose of 1 capsule/day over two weeks. This test was carried out in the autumn season (October) where the decrease in the atmospheric temperature and the dryness of the air proceeded. A treatment of forcibly irradiating each of the subjects with ultraviolet ray was not carried out.

The lightness (L value) of the left cheek of each of the subjects was evaluated before and after the ingestion. The L value was measured by subjecting each of the subjects to face washing in a room which was conditioned at a room temperature of 21±1° C. and a room temperature of 50±5%, then allowing each of the subjects to wait for 10 minutes, and then measuring the lightness of the left cheek of each of the subjects using a lightness measuring device (a spectrophotometer CM-2600d; manufactured by Konica Minolta Optics, Inc.). An average value of the L values measured in each of the test food ingestion group (22 persons) and the placebo food ingestion group (21 persons) before and after the ingestion was determined. As the evaluation on effectiveness, the comparison over time in each of the groups (i.e., within group comparison) was carried out employing paired t-test.

TABLE 1

| 30- to 49-years-old | L value | | |
|---|---|---|---|
| | Before ingestion | Two weeks after ingestion | p |
| Test food (22 persons) | 62.76 | 62.73 | No significant change was observed |
| Placebo food (21 persons) | 62.32 | 62.16 | Significant decrease was observed ($p < 0.05$)* |

*Compared before and after ingestion (paired t-test)

As shown in Table 1, in the placebo food ingestion group, remarkable and significant decrease in the L value was observed after the ingestion compared with that before the ingestion ($p<0.05$). In contrast, in the test food ingestion group, significant decrease in the L value was not observed after the ingestion compared with that before the ingestion. It was shown that the paprika extract exerted an effect to suppress the decrease in skin lightness (i.e., the progression of dullness) that was observed in the placebo ingestion group.

Example 3

Twenty persons (specifically 42- to 49-year-old persons), who were in an older age group, were selected from the whole population (43 persons) employed in Example 2, and an average value of the L values before and after the ingestion was determined in each of a test food ingestion group (10 persons) and a placebo food ingestion group (10 persons) in the same manner as in Example 2. As the evaluation on effectiveness, the comparison over time in each of the groups (i.e., within group comparison) was carried out employing paired t-test.

TABLE 2

| 42- to 49-years-old | L value | | |
|---|---|---|---|
| | Before ingestion | Two weeks after ingestion | p |
| Test food (10 persons) | 61.36 | 61.38 | No significant change was observed |
| Placebo food (10 persons) | 61.79 | 61.62 | Significant decrease was observed ($p < 0.05$)* |

*Compared before and after ingestion (paired t-test)

As shown in Table 2, when the whole population in Example 2 was narrowed down to an older age group, in the placebo food ingestion group, the degree of the decrease in the L value after the ingestion compared with that before the ingestion was expanded compared with that in Example 2. In the test food ingestion group, in contrast, improvement in the L value was observed compared with that measured before the ingestion. That is, when the whole population was narrowed down to the older age group, the variation in the L value was further expanded compared with that in the whole population employed in Example 2. With respect to the change in the L value before and after the ingestion, significant decrease ($p<0.05$) was confirmed only in the placebo food ingestion group. From these results, it was demonstrated that the paprika extract exerted a higher dullness suppressing effect in the persons in the older age group who were more susceptible to dullness.

Example 4

A transepidermal water loss (TEWL) before and after the ingestion was measured in each of the test food ingestion group and the placebo food ingestion group employed in Example 2. The TEWL value was determined by subjecting each of the subjects to face washing in a room which was conditioned at a room temperature of 21±1° C. and a humidity of 50±5%, then allowing each of the subjects to wait for 10 minutes, and then measuring the transepidermal water loss on the left cheek of each of the subjects using a transepidermal water loss measuring device (Vaposcan; manufactured by Asahi Techno Lab. ltd.).

An average value of the TEWL values measured before and after the ingestion in each of the test food ingestion group (22 persons) and the placebo food ingestion group (21 persons) was determined. As the evaluation on effectiveness, the comparison over time in each of the groups (i.e., within group comparison) was carried out employing paired t-test.

TABLE 3

| 30- to 49-years-old | TEWL value ($g/h \cdot m^2$) | | |
|---|---|---|---|
| | Before ingestion | Two weeks after ingestion | p |
| Test food (22 persons) | 12.51 | 13.42 | No significant change was observed |
| Placebo food (21 persons) | 11.44 | 12.86 | Significant decrease was observed ($p < 0.05$)* |

*Compared before and after ingestion (paired t-test)

As shown in Table 3, in the placebo food ingestion group, remarkable and significant increase in the transepidermal water loss was observed after the ingestion compared with that before the ingestion ($p<0.05$). In contrast, in the test food ingestion group, significant increase in the transepidermal water loss was not observed after the ingestion compared with that before the ingestion. It was shown that the paprika extract exerted an effect to suppress the deterioration in the skin barrier function which was observed in the placebo ingestion group.

Example 5

Twenty persons (30- to 40-year-old persons), who were in a younger to middle age group, were selected from the whole population (43 persons) employed in Example 2, and an average value of the TEWL values before and after the ingestion in each of a test food ingestion group (11 persons) and a placebo food ingestion group (9 persons) was determined in the same manner as in Example 4. As the evaluation on effectiveness, the comparison over time in each of the groups (i.e., within group comparison) was carried out employing paired t-test.

TABLE 4

| 30- to 40-years-old | TEWL value (g/h · $m^2$) | | |
|---|---|---|---|
| | Before ingestion | Two weeks after ingestion | p |
| Test food (11 persons) | 11.53 | 11.62 | No significant change was observed |
| Placebo food (9 persons) | 11.91 | 14.34 | Significant decrease was observed ($p < 0.05$)* |

*Compared before and after ingestion (paired t-test)

As shown in Table 4, when the whole population in Example 2 was narrowed down to the younger to middle age group, in the placebo food ingestion group, the degree of the increase in the TEWL value after the ingestion compared with that before the ingestion was increased compared with that in Example 4. In the test food ingestion group, in contrast, the degree of the increase in the TEWL value was decreased compared with that measured before the ingestion. That is, when the whole population was narrowed down to the younger to middle age group, the variation in the TEWL value was further expanded compared with that in the whole population employed in Example 2. With respect to the change in the TEWL value before and after the ingestion, a significant difference ($p<0.05$) was confirmed only in the placebo food ingestion group. From these results, it was demonstrated that the paprika extract exerted a higher skin barrier maintaining or improving effect in the persons in the younger to middle age group who were particularly susceptible to a factor involved in the deterioration in the skin barrier function.

As in the case of Examples 2 to 5, the red paprika extract-containing soft capsules (a total color value per capsule: 270) prepared using the red paprika extract (a color value: 660) prepared in Example 1 also exerted an effect to suppress the decrease in skin lightness (i.e., the progression in dullness), a higher dullness suppressing effect in persons in an older age group who were more susceptible to dullness, an effect to suppress the deterioration in the skin barrier function, and a higher skin barrier maintaining or improving effect in persons in a younger to middle age group who were particularly susceptible to a factor involved in the deterioration in the skin barrier function.

The preferred embodiments of the present invention are as mentioned above. However, the present invention is not intended to be limited to these embodiments, and various other embodiments may be made without departing from the spirit of the invention.

What is claimed is:

1. A method of maintaining or improving a skin barrier function in a subject in need thereof comprising orally administering to the subject an effective amount of a composition comprising a hexane extract from red paprika, wherein the hexane extract is not obtained by using acetone or methanol as an extraction solvent, wherein the hexane extract contains a hexane-soluble component selected from the group consisting of a xanthophyll and p-carotene, wherein the xanthophyll is selected from the group consisting of capsanthin, cucurbitaxanthin A, zeaxanthin, capsanthin 3, 6-epoxide, capsorubin, cryptocapsin and a derivative thereof, wherein the derivative is a fatty acid ester of a saturated fatty acid having 12 to 22 carbon atoms.

2. The method of claim 1, wherein trans-epidermal water loss (TEWL) is reduced in the subject.

3. The method according to claim 1, wherein the subject is administered a dose of 10 to 400 mg/day of the hexane extract.

4. The method according to claim 1, wherein the color value (E 10% 1 cm) of the composition is 0.1 to 3500.

5. The methods according to claim 1, wherein the composition is a dietary supplement, a food or a beverage.

6. The method according to claim 5, wherein the composition comprises a food-hygienically acceptable additive.

7. The method according to claim 6, wherein the food-hygienically acceptable additive is selected from the group consisting of a sweetener, an acidulant, an excipient, a dextrin, a starch, a binder, a diluent, an oil, a fat, a flavoring material, a coloring agent, a buffering agent, a thickening agent, a gelatinizing agent, a stabilizing agent, a preservative agent, an emulsifying agent, a dispersing agent, a suspending agent and an antiseptic agent.

8. The method according to claim 1, wherein the composition is in a form of a tablet, a hard capsule, a soft capsule, a beverage, an original liquid concentrate, an instant powder for a beverage, an oil, a fat, an oil and fat processed food and a seasoning agent.

9. The method according to claim 7, wherein the sweetener is selected from the group consisting of glucose, sucrose, fructose, high-fructose corn syrup, aspartame and stevia.

10. The method according to claim 7, wherein the acidulant is selected from the group consisting of citric acid, malic acid and tartaric acid.

11. The method according to claim 1, wherein the saturated fatty acid is lauric acid, myristic acid, palmitic acid, stearic acid or oleic acid.

12. The method of claim 1, wherein the hexane-soluble component comprises cucurbitaxanthin A and/or capsanthin 3,6-epoxide.

* * * * *

UNITED STATES PATENT AND TRADEMARK OFFICE

CERTIFICATE OF CORRECTION

PATENT NO. : 11,957,780 B2
APPLICATION NO. : 17/449701
DATED : April 16, 2024
INVENTOR(S) : Kazuhisa Sugimoto It is certified that error appears in the above-identified patent and that said Letters Patent is hereby corrected as shown below:

In the Specification

In Column 5, Line 12, delete "ramyuro-" and insert --ramiro- --.

In the Claims

In Column 14, Claim 4, Line 20, delete "(E 10% 1 cm)" and insert --($E^{10\%}_{1cm}$)--.

In Column 14, Claim 5, Line 21, delete "methods" and insert --method--.

Signed and Sealed this
Second Day of July, 2024

Katherine Kelly Vidal

Katherine Kelly Vidal
*Director of the United States Patent and Trademark Office*